United States Patent [19]

Lord et al.

[11] 4,281,929

[45] Aug. 4, 1981

[54] SMALL DIAMETER, DEEP BORE OPTICAL INSPECTION SYSTEM

[75] Inventors: David E. Lord; Richard R. Petrini; Gary W. Carter, all of Livermore, Calif.

[73] Assignee: The United States of America as represented by the United States Department of Energy, Washington, D.C.

[21] Appl. No.: 39,985

[22] Filed: May 17, 1979

[51] Int. Cl.³ .............................................. G01N 21/01
[52] U.S. Cl. .................................. 356/241; 350/96.26
[58] Field of Search ....................... 356/241; 350/96.26

[56] References Cited

U.S. PATENT DOCUMENTS

| 3,221,593 | 12/1965 | Ferris | 356/241 |
| 3,413,067 | 11/1968 | Froio | 356/241 |
| 4,072,427 | 2/1978 | Alsberg | 356/241 |

OTHER PUBLICATIONS

Report UCRL-52431 by D. E. Lord et al., Entitled "Optical Inspection of Small Diameter Deep Bores Using Rod Optics With Low-Light Television & Still Photography" Feb. 22, 1978.
Design News/11-20-78/63, "Mirror, Rod Optics Inspect Deep Bores"; R. F. Stengel, Westerner Editor.

*Primary Examiner*—Vincent P. McGraw
*Attorney, Agent, or Firm*—L. E. Carnahan; Roger S. Gaither; James E. Denny

[57] ABSTRACT

An improved rod optic system for inspecting small diameter, deep bores. The system consists of a rod optic system utilizing a curved mirror at the end of the rod lens such that the optical path through the system is bent 90° to minimize optical distortion in examining the sides of a curved bore. The system is particularly useful in the examination of small bores for corrosion, and is capable of examining 1/16 inch diameter and up to 4 inch deep drill holes, for example. The positioning of the curved mirror allows simultaneous viewing from shallow and right angle points of observation of the same artifact (such as corrosion) in the bore hole. The improved rod optic system may be used for direct eye sighting, or in combination with a still camera or a low-light television monitor; particularly low-light color television.

11 Claims, 6 Drawing Figures

SMALL DIAMETER, DEEP BORE OPTICAL INSPECTION SYSTEM

BACKGROUND OF THE INVENTION

The invention described herein arose under work at the Lawrence Livermore Laboratory in the course of, or under, Contract No. W-7405-ENG-48 between the University of Califorina and the U.S. Department of Energy.

This invention relates to rod optic systems, and more particularly to an improved rod optic system for inspecting small diameter, deep bore holes.

Various types of endoscopes, borescopes, and the like which employ fiber optics, light illumination, mirrors, lens and like optics are known in the art as exemplified by U.S. Pats. No. 2,541,976 issued Feb. 20, 1951; U.S. Pat. No. 2,849,530 issued Aug. 26, 1958; U.S. Pat. No. 2,959,089 issued Nov. 8, 1960; U.S. Pat. No. 2,987,960 issued June 13, 1961; U.S. Pat. No. 3,279,460 issued Oct. 18, 1966; U.S. Pat. No. 3,297,022 issued Jan. 10, 1967; and U.S. Pat. No. 4,102,582 issued July 25, 1978. In addition, the use of cameras or television monitors for recording information viewed by the endoscopes or borescopes are known as exemplified by above-cited U.S. Pats. No. 2,849,530; U.S. Pat. No. 3,279,460; and U.S. Pat. No. 4,102,582.

Various uses for rod optics systems are known in the art, which range from dynamic flow observations to internal inspection of small welded bellows. These systems utilize a rod optic or lens from 0.10 to 0.25 inch in diameter and 4 to 18 inches long. These prior rod optics systems are coupled to low-light black-and-white video systems and conventional still cameras. Also, rod optics systems having diameters as small as 0.067–0.087 inches have been recently developed for small diameter bore inspection applications.

A rod lens, as known in the art, is many times longer than its unusually small diamter. It is designed to transmit as much light as possible from the viewed object. This light, reflected by the object from the light source, contains the information or intelligence regarding that object. Because the reflected light that finds its way into the rod lens is usually several orders of magnitude less than the incident light, it must be transmitted as loss-free as possible. Thus, modern rod optical systems are designed to retrieve as much reflected light as possible. The basic features of such systems are an intense light source whose light is transmitted through a bundle of glass fibers to the object to be viewed and light reflected from that object is transmitted through a rod lens to a viewer. Such a system allows access to difficult-to-view volumes through very small aperatures. The main disadvantage of these systems is the small, long aperture the reflected light must traverse and consequently the very low amount of intelligence-carrying light that makes the return trip. Two additional factors which help to increase the efficiency of the system are: (b) the increased incident illumination using high-intensity quartz halogen lamp, and (2) the sensitivity of the viewer's eye is augmented by fast-response photographic film or super sensitive video systems. While the prior art rod lens systems are effective, they are not capable of inspecting small diameter holes below 0.067 inches in diameter, such as bore holes of 1/16 inch (0.0625 in) diameter having a depth of 2 to 4 inches. Nor can the prior art systems minimize optical distortion in examining the sides of a curved bore. Also, the prior art systems cannot observe artifacts, such as corrosion, from both shallow and right angle points of view simultaneously.

SUMMARY OF THE INVENTION

The present invention is an improved rod optic system capable of inspecting a 2–4 inch deep, 1/16 (0.0625) inch diameter drill holes while both minimizing optical distortion and examining the sides of a curved bore. The improved system has the additional capability of simultaneous viewing of artifacts from two different viewing angles. The rod optic system of the present invention basically constitutes a modification of an existing rod optic system plus the addition of a curved mirror arrangement. The system may utilize direct sighting for inspection of the bore hole, or utilize a still camera or a television monitor, particularly color television, to record the inspected service area of the bore hole. The system utilizes a curved, inclined mirror located near the exterior end of the rod lens to minimize optical distortion while examining the curved side surfaces of a drill hole and permits viewing artifacts, such as corrosion, from both shallow and right angles of observation.

Therefore, it is an object of the invention to provide an improved rod optic system for inspecting small diameter bore holes.

A further object of the invention is to provide an improved rod optic system for inspecting drill holes having a depth of up to four inches and a diameter of about 1/16 (0.0625) inch.

Another object of the invention is to provide a small diameter rod optic system compatible with either a still camera or a television monitor system, particularly low-light color television, or which can be utilized by direct sighting.

Another object of the invention is to provide an improved rod optic system capable of minimizing optical distortion in examining the sides of a curved bore by incorporating a curved mirror adjacent to he end of the rod lens of the optics system.

Another object of the invention is to simultaneously view artifacts from two angular points of view.

Other objects of the invention will become readily apparent to those skilled in the art from the following description and accompanying drawings.

DETAILED DESCRIPTION OF THE INVENTION

The present invention involves an improved rod optics system which can be used by direct sighting or coupled with a still camera or with a low-light video system. Such rod optic systems have a variety of applications from the measurement of dynamic fluid flow to the inspection of inaccessible areas for contamination and corrosion. This system of this invention is particularly applicable for low-light color imagery which greatly enhances the sensitivity of the presentation.

The rod optic system of this invention has particular application for corrosion inspection of small bore holes--those having a length of under 4 inches and a diameter of about 1/16 inch. In addition, the optic system of the present invention minimizes optical distortion when examining the sides of a curved bore by fitting the forward end of the probe with a curved mirror inclined at about a 45° angle to the longitudinal axis of the probe. It also provides for simultaneous viewing at shallow and right angles of artifacts by positioning the curved mirror along the probe axis.

Figure 1:
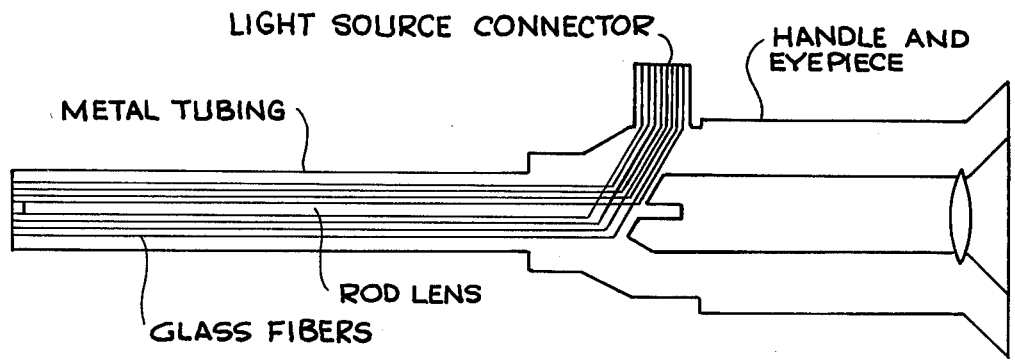
FIG. 1 is a schematic diagram of a typical prior art rod optic system.

FIG. 1 illustrates a typical prior art rod optic system such as the Japenese made Olympus-Selfoc system having a probe diameter as small as 0.067 inch. The basic features of the FIG. 1 system are, as indicated by legend, a handle and eye piece having a metal tubing secured to the forward end forming a probe within which is centrally mounted a rod lens, with glass fibers which transmit light from a light source connector to the forward end of the metal tube filling an annulus between the rod lens and the metal tubing. The light source connector is connected to an intense light source, such as a quartz halogen lamp. Thus, illumination light is transmitted to the object to be viewed through the fibers and reflected light is returned to the viewer through the rod lens system.

Figure 2:
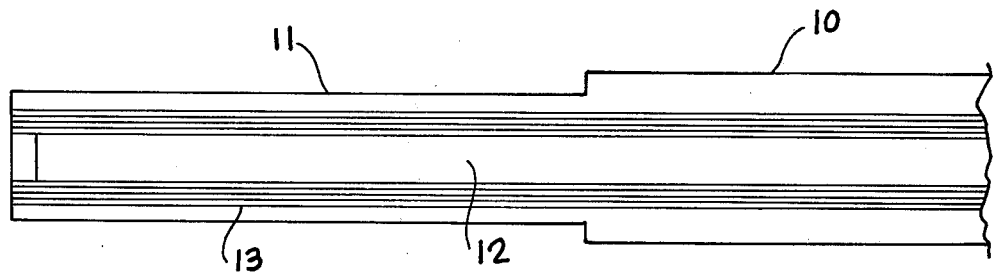
FIG. 2 illustrates the modification of the metal tubing of the FIG. 1 system to reduce the diameter thereof in accordance with the invention.
Figure 3:
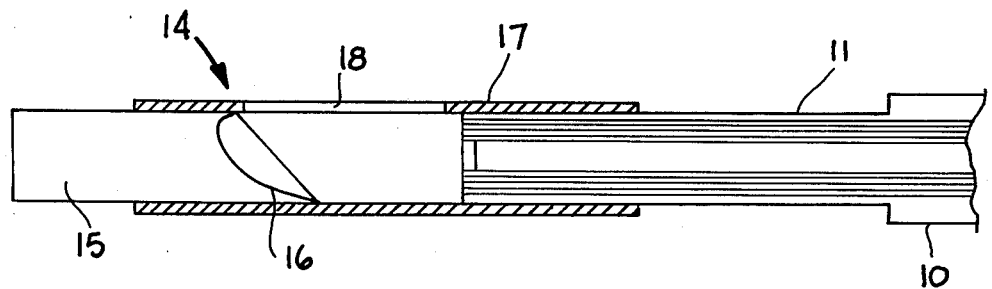
FIG. 3 illustrates the curved mirror attachment to the reduced diameter end of the FIG. 1 system in accordance with the invention.

FIGS. 2 and 3 illustrate the modifications to the FIG. 1 rod optic system to enable it to be utilized for inspecting the wall surfaces of bore holes smaller in diameter than the probe section of the FIG. 1 system. The smallest diamter rod optic system known, prior to this invention, is the above-referenced Olympus-Selfoc system, illustrated in FIG. 1 wherein the metal tubing or probe has a 0.067 inch external diameter, and thus cannot be used to inspect a 1/16 (0.0625) inch or smaller drill hole. The invention described herein involves an embodiment for inspection of a 1/16 diameter hole having a depth of 2 to 4 inches, but smaller diameters and greater depths can be examined utilizing the basic principle of the invention as described hereinafter. The metal tubing or probe section of the FIG. 1 system has a length of about four (4) inches and an outer diameter of 0.067 inch. As shown enlarged in FIG. 2, the metal tubing 10 composed of stainless steel, is provided with a reduced diameter section 11 (outer diameter of 0.054 inch) with a rod lens 12 having a 0.037 inch diameter, and the annulus between tubing 10 and lens 12 being filled with glass fibers 13 as in the FIG. 1 system. The reduced section 11 is produced by electroetching or milling away the outer surface of the metal tubing. The electroetching process may utilize phosphoric acid in the electrochemical cell and was done over the outer two (2) inches of the metal tube 10. It is seen that section 11 can be further reduced in diameter provided the remaining material of metal tube 10 has sufficient structural thickness to support the rod lens and glass fibers.

As shown in FIG. 3, the system of FIG. 2 is modified by the addition of a curved mirror assembly, generally indicated at 14, at the outer end of the probe or metal tube 10 which functions to minimize optical distortion when examining the sides of a curved bore or drill hole. The mirror assembly 14 consists of a rod 15, such as a 0.054 inch stainless steel, having a curved polished surface 16 defining a mirror and mounted within a sleeve 17, such as brass having a 0.003 inch wall thickness and length of ¼ inch, which is secured to section 11 of metal tubing 10. Sleeve 17 is provided with a slot 18 (length of ¼ inch and width of 0.054) adjacent mirror or curved surface 16 of rod 15. The outer diameter of sleeve 17 is 0.057 inch which can be readily inserted into a 0.0625 inch drill hole, for example. The mirror or curved surface 16 is inclined at a 45° angle so that the optical path of light traveling through the system is bent 90°. The curvature of the curved surface 16 approximates the curvature of the bore being inspected. The mirror not only changes the viewing angle within the bore, but it also changes the incident light distribution. Without the mirror, the shallow angle of the incident light greatly accentuated bore roughness. With the mirror the illumination level is greatly increased, an important factor in photographic exposures, and softens the harsh shadows caused by bore roughness. The mirror and sleeve can be positioned on the modified rod optic to provide a combined shallow and right angle view or an all-right angle view.

Figure 4:
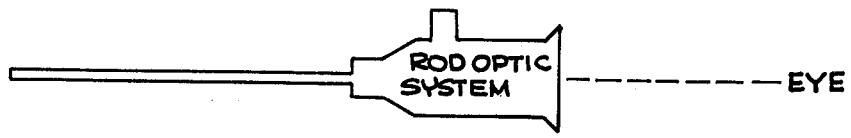
FIGS. 4–6 illustrates readout means utilizing the rod optic system of the invention.
Figure 5:
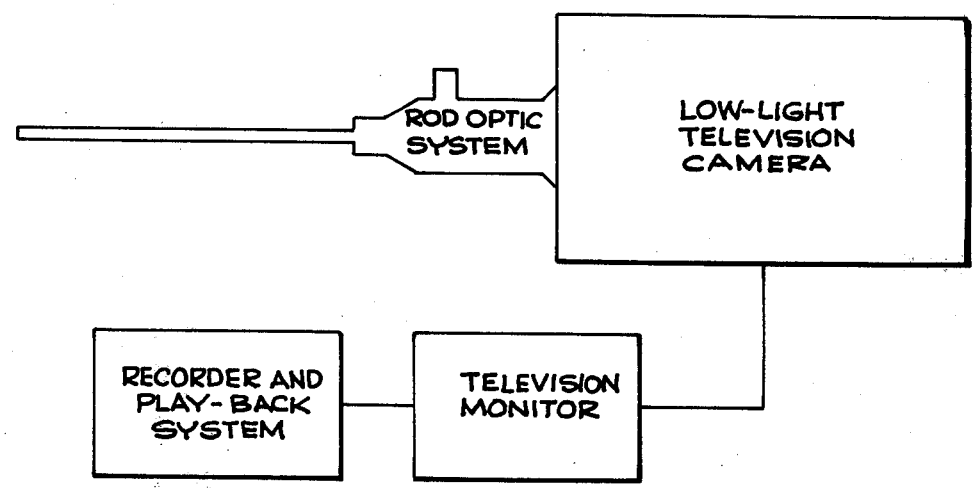
Figure 6:
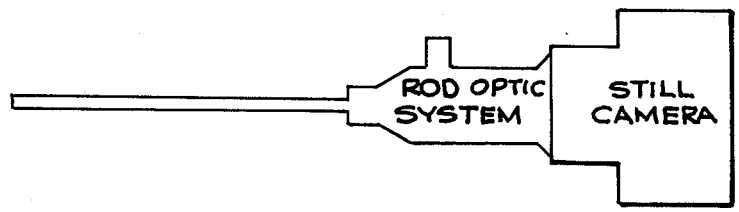

The improved rod optic system of this invention may be used in combination with the human eye for direct sighting as shown in FIG. 4, with a low-light video system (television monitor, both in color and black-and-white) as shown in FIG. 5, or with a still camera as shown in FIG. 6. The system is particularly applicable for low-light color video systems as described in the hereinafter referenced publications.

Tests conducted on the above-described embodiment of the invention have shown excellent results and particularly verified the corrosion detection capability of the improved rod optic system. Such results were unobtainable with the available rod optics systems. A description of the construction details and test results of the above-described embodiment of this invention are set forth in report UCRL-52431 by D. E. Lord, et al., published May 26, 1978 and in an article entitled "Mirror Rod Optics Inspect Deep Bores," by R. F. Stengel, Western Editor, published in Design News/11-20-78/63. The inventors of this invention are three of the four coauthors of the report UCRL-52431, and the Design News article was written after the release of this report.

In summary, the present invention provides the capability to inspect small diameter, deep bores to an extent not previously available, as was recognized by the Design News article. This combination minimizes the illumination problems of looking into a "blind hole" by utilizing an external light sources. The ability to increase the intensity of this light source permits the presentation of color imagery which enhances the sensitivity of the presentation and, in some cases, permits the source or composition of the corrosion or impurity to be identified, as clearly illustrated in above-referenced report UCRL-52431. Optical resolution is greatly enhanced by means of the novel mirror system incorporated into the rod optics which results in a 90° bend in the optical path through the system.

The invention thus provides a system which is unparalleled for the detection of corrosion deposits from the standpoints of color representations and the shallow and right angle viewing which provides a near three dimensional viewing and evaluation capability. The improved rod optic system in combination with a low-light color video system is economically advantageous for technical reasons and for human engineering reasons, and it is easier to use than prior known systems.

While a particular embodiment of the invention has been illustrated and described, modifications will become apparent to those skilled in the art, and it is intented to cover in the appended claims all such modifications as come within the spirit and scope of the invention.

What we claim is:

1. Apparatus for viewing a small diameter, deep bore with minimal optical distortion comprising: a small-diameter rod optic system having a rod lens, a curved mirror having a single inclined convex surface and a diameter approximately equal to that of the rod optic system, said inclined convex surface extending at an angle to the longitudinal axis of the rod lens, and means having a slot therein adjacent said curved mirror for mounting the curved mirror in spaced relationship to the rod lens and at an end of the rod lens which is located at one end of the rod optic system so that light traveling through the rod optic system is bent about an angle of 90° by the curved mirror.

2. The apparatus defined in claim 1, further in combination with a low-light color video system, said video system being connected to receive an optical input from said rod optic system.

3. The apparatus defined in claim 1, further in combination with a camera, said camera being positioned so as to receive optical information transmitted by said rod lens of said optic system.

4. In a rod optic system comprising metal tubing defining a probe, a rod lens centrally located in the metal tubing, glass fibers within the metal tubing and surrounding the rod lens, wherein light from a source is directed through the glass fibers to an object to be viewed and light reflected from an object to be viewed is transmitted through the rod lens; the improvement consisting of: means for minimizing optical distortion when examining sides of a curved bore and being capable of providing simultaneous viewing at shallow and right angles of artifacts in a curved bore, said means including a curved mirror having a single inclined convex surface and positioned adjacent to and in axial alignment with an outer end of said rod lens such that light traveling through the rod optic system is bent about an angle of 90° by said curved mirror, said inclined convex surface of said mirror being at about 45° to the longitudinal axis of the rod lens, and means having an opening therein adjacent said curved mirror for retaining said curved mirror adjacent said rod lens.

5. The improvement defined in claim 4, wherein said retaining means for said curved mirror consists of a sleeve connected to an outer end of the metal tubing of the rod optics system, said sleeve having a diameter not greater than the metal tubing, and wherein said opening consists of a slot in said sleeve adjacent said curved mirror.

6. The improvement defined in claim 5, wherein said curved mirror comprises a rod having a polished convex end surface thereof cut at an inclined angle of about 45° to the longitudinal axis of the rod to define a curved mirror surface.

7. The improvement defined in claim 5, wherein said sleeve has an outer diameter of less than about 0.0625 inches, and wherein an end portion of the metal tubing of the rod optic system has a diameter less than 0.0625 inch.

8. A method for inspecting bore holes having a diameter of no greater than about 0.0625 inch while minimizing optical distortions comprising of the steps of: forming at least a portion of a probe of a rod optic system so as to define a diameter less than about 0.0625 inches, and providing a curved mirror assembly having a single inclined convex surface adjacent an outer end of the probe and of about the same diameter as the probe to increase the intensity of the light transmitted through the rod optics system.

9. The method defined in claim 8, additionally including the step of forming the curved mirror to define an angle inclined at 45° with respect to the longitudinal axis of the probe.

10. The method defined in claim 8, additionally including the step of providing means operatively connected to the rod optic system to view surfaces of an inspected bore hole.

11. The method defined in claim 8, additionally including the step of positioning the inclined convex surface of the curved mirror so as to provide simultaneous viewing of artifacts in a bore hole at shallow and right angles of observation or at a total right angle view.

* * * * *